United States Patent [19]

Schmidt et al.

[11] 4,255,577

[45] Mar. 10, 1981

[54] PROCESS AND INTERMEDIATES FOR PREPARING 3-[4-(DISUBSTITUTED-AMINO)PHENYL] OR (9-JULOLIDINYL)-3-(DI-PHENYLAMINO)PHTHALIDES

[75] Inventors: Paul J. Schmidt, Sharonville; William M. Hung, Cincinnati, both of Ohio

[73] Assignee: Sterling Drug Inc., New York, N.Y.

[21] Appl. No.: 69,979

[22] Filed: Aug. 27, 1979

Related U.S. Application Data

[60] Division of Ser. No. 19,594, Mar. 12, 1979, Pat. No. 4,200,313, which is a division of Ser. No. 942,996, Sep. 18, 1978, Pat. No. 4,187,223, which is a continuation-in-part of Ser. No. 821,927, Aug. 4, 1977, Pat. No. 4,168,378, which is a continuation-in-part of Ser. No. 755,183, Dec. 29, 1976, abandoned.

[51] Int. Cl.$^3$ .................... C07D 307/83; C07D 455/00
[52] U.S. Cl. ................. 546/94; 260/343.3 R; 562/441
[58] Field of Search ................. 260/343.3 R; 562/441; 546/94

[56] References Cited

U.S. PATENT DOCUMENTS

| | | | |
|---|---|---|---|
| 2,834,788 | 5/1958 | Wheeler et al. | 260/343.3 R |
| 2,861,082 | 11/1958 | Wheeler et al. | 260/343.3 R |
| 2,989,541 | 6/1961 | Wheeler et al. | 260/343.3 R |
| 2,997,481 | 8/1961 | Weeler et al. | 260/343.3 R |
| 3,829,322 | 8/1974 | Ozutsumi et al. | 260/343.3 R |
| 3,919,303 | 11/1975 | Schuhmacher et al. | 562/441 |
| 3,925,457 | 12/1975 | Tsunemitsu et al. | 562/441 |
| 4,007,195 | 2/1977 | Garner et al. | 260/326.5 CA |
| 4,036,855 | 7/1977 | Houlihan | 260/343.3 R |
| 4,096,176 | 6/1978 | Crounse et al. | 260/326.47 |

FOREIGN PATENT DOCUMENTS

| | | | |
|---|---|---|---|
| 2537776 | 3/1976 | Fed. Rep. of Germany | 260/343.4 |
| 46-16 | 2/1971 | Japan | 260/343.3 R |

*Primary Examiner*—Henry R. Jiles
*Assistant Examiner*—Jane T. Fan
*Attorney, Agent, or Firm*—Paul E. Dupont; B. Woodrow Wyatt

[57] ABSTRACT

3-[4-(Disubstituted-amino)phenyl] or (9-julolidinyl)-3-(diphenylamino)phthalides useful as color formers in pressure-sensitive and thermal marking systems are prepared by reaction of 2-[4-(disubstituted-amino)benzoyl] or (9-julolidinyl-carbonyl)benzoic acids with diphenylamines.

6 Claims, No Drawings

PROCESS AND INTERMEDIATES FOR PREPARING 3-[4-(DISUBSTITUTED-AMINO)PHENYL] OR (9-JULOLIDINYL)-3-(DIPHENYLAMINO)PHTHA- LIDES

This application is a division of application Ser. No. 19,594 filed Mar. 12, 1979 now U.S. Pat. No. 4,200,313 issued Apr. 29, 1980, in turn a division of application Ser. No. 942,996 filed Sept. 18, 1978, now U.S. Pat. No. 4,187,223 issued Feb. 5, 1980, in turn a continuation-in-part of application Ser. No. 821,927 filed Aug. 4, 1977, now U.S. Pat. No. 4,168,378 issued Sept. 18, 1979, in turn a continuation-in-part of application Ser. No. 755,183 filed Dec. 29, 1976 and now abandoned.

BACKGROUND OF THE INVENTION

1. Field of the Invention

This invention relates to a group of compounds classified in the field or organic chemistry as 3-[4-(disubstituted amino)phenyl] or (9-julolidinyl)-3-(diphenylamino)phthalides useful in the art of carbonless duplicating as color formers in pressure-sensitive and thermal marking systems; to processes for the preparation thereof; and to pressure-sensitive duplicating systems and thermal marking systems containing the same.

2. Description of the Prior Art

Several classes of organic compounds of widely diverse structural types are known to be useful as color formers for carbonless duplicating systems. Among the more widely recognized classes, there may be named phenothiazines, for example, benzoyl leuco methylene blue; fluorans, for example, 2'-anilino-6'-diethylaminofluoran; phthalides, the class with which this invention is concerned, for example, crystal violet lactone; and various other types of color formers currently employed in commercially accepted carbonless duplicating systems. Typical of the many such systems taught in the prior art are those described in U.S. Pat. Nos. 2,712,507, 2,800,457 and 3,041,289 which issued July 5, 1955 and June 26, 1957 and June 26, 1962, respectively. Many of the color formers in the prior art suffer one or more disadvantages such as low tinctorial strength, poor light stability, low resistance to sublimation and low solubility in common organic solvents, the latter disadvantage thus requiring the use of specialized and expensive solvents in order to obtain microencapsulated solutions of sufficient concentration for use in pressure-sensitive copying systems.

The following appear to constitute the most relevant prior art relative to the present invention.

Japanese Patent Publication No. 71/4616 published Feb. 4, 1971 discloses a series of compounds having the formula

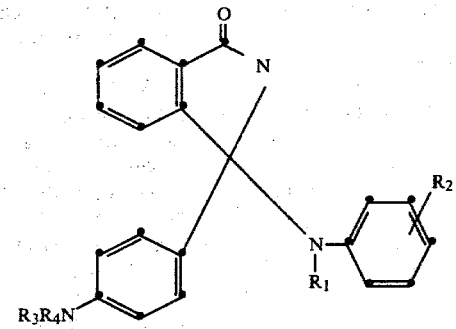

wherein $R_1$ is hydrogen or lower-alkyl; $R_2$ is hydrogen, halogen or lower-alkyl; and $R_3$ and $R_4$ are each lower-alkyl. The compounds are prepared by reaction of a 2-[4'-(dialkylamino)benzoyl]benzoic acid with an appropriate aniline, and are stated to be useful as color formers in pressure-sensitive copying paper.

R. Valters and V. Tsiekure in Khim. Geterotsikl. Soedin. 1975, (11) 1476–8 discuss ring-chain tautomerism in 3-(N,N-diphenylamino)-3-phenylphthalide but disclose no utility for the compound.

3. Patent Activities of Others

German Offenlegungsschrift No. 2,537,776 published Mar. 11, 1976, based on Japanese Application No. 97934-74 published Mar. 2, 1976 as Japanese Patent Publication No. 76/25529, discloses in most pertinent part a series of phthalides stated to be useful as color formers and having the formula:

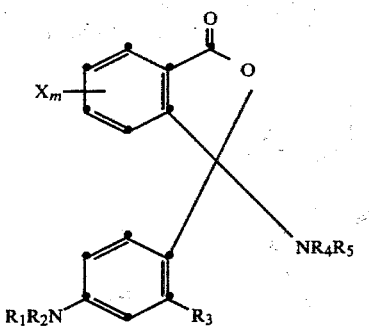

wherein inter alia $R_1$ and $R_2$ are the same or different and are lower-alkyl, a benzyl group which can be substituted in its aromatic ring with a di-lower-alkylamino group having 1 to 4 carbon atoms in its alkyl portions; or a phenyl group which can be substituted with a lower-alkoxy group with 1 to 4 carbon atoms; $R_3$ is a chlorine atom, a lower-alkyl group with 1 to 4 carbon atoms or a lower-alkoxy group with 1 to 4 carbon atoms; $R_4$ is hydrogen or a lower-alkyl group with 1 to 4 carbon atoms; $R_5$ is a phenyl group which can be substituted with a lower-alkyl group of 1 to 4 carbon atoms or a chlorine atom.

SUMMARY OF THE INVENTION

The present invention provides novel 3-[4-(disubstitutedamino] or (9-julolidinyl)-3-(diphenylamino)phthalides useful as color formers in pressure-sensitive duplicating systems and thermal marking systems. The compounds develop colored images of good to excellent tinctorial strength, and have the advantages of improved light stability, high resistance to sublimation and enhanced solubility in common organic solvents.

In a composition-of-matter aspect the invention relates to a series of 3-(2-$R_1$-4-$NR_2R_3$-phenyl) or (9-julolidinyl)-3-[N-($Y_1$-$Y_2$-phenyl)-N-($Y_3$-$Y_4$-phenyl-)amino]-4-$Q_4$-5-$Q_5$-6-$Q_6$-7-$Q_7$-phthalides which are useful as color formers in pressure-sensitive carbonless duplicating systems or thermal marking systems.

In a process aspect the present invention provides a process for preparing 3-(2-$R_1$-4-$NR_2R_3$-phenyl) or (9-julolidinyl)-3-[N-($Y_1$-$Y_2$-phenyl)-N-($Y_3$-$Y_4$-phenyl-)amino]-4-$Q_4$-5-$Q_5$-6-$Q_6$-7-$Q_7$-phthalides which comprises reacting a 2-(2-$R_1$-4-$NR_2R_3$-benzoyl) or (9-julolidinylcarbonyl)-4-$Q_4$-5-$Q_5$-6-$Q_6$-7-$Q_7$-benzoic acid with a N-($Y_1$-$Y_2$-phenyl)-N-($Y_3$-$Y_4$-phenyl)amine.

This invention further provides a second process for preparing 3-(2-$R_1$-4-$NR_2R_3$-phenyl) or (9-julolidinyl)-3-[N-($Y_1$-$Y_2$-phenyl)-N-($Y_3$-$Y_4$-phenyl)amino]-4-$Q_4$-5-$Q_5$-6-$Q_6$-7-$Q_7$-phthalides which comprises reacting a 2-(2-$R_1$-4-$NR_2R_3$-benzoyl) or (9-julolidinylcarbonyl)-4-$Q_4$-5-$Q_5$-6-$Q_6$-7-$Q_7$-benzoic acid with an inorganic acid chloride followed by reaction of the product so-obtained with a N-($Y_1$-$Y_2$-phenyl)-N-($Y_3$-$Y_4$-phenyl)amine.

In an article-of-manufacture aspect the present invention relates to a pressure-sensitive carbonless duplicating system or thermal marking system containing a color-forming substance comprising a 3-(2-$R_1$-4-$NR_2R_3$-phenyl) or (9-julolidinyl)-3-[N-($Y_1$-$Y_2$-phenyl)-N-($Y_3$-$Y_4$-phenyl)amino]-4-$Q_4$-5-$Q_5$-6-$Q_6$-7-$Q_7$-phthalide.

DETAILED DESCRIPTION INCLUSIVE OF THE PREFERRED EMBODIMENTS

More specifically, this invention in a composition-of-matter aspect resides in a compound having Formula I

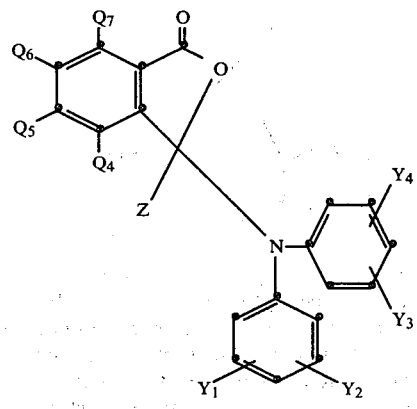

Formula I wherein:
$Q_4$ is hydrogen or halo;
$Q_5$ is the same as $Q_4$; or di-lower-alkylamino, COX or halo when $Q_4$, $Q_6$ and $Q_7$ are each hydrogen;
$Q_6$ is the same as $Q_4$; or di-lower-alkylamino, COX or halo when $Q_4$, $Q_5$ and $Q_7$ are each hydrogen;
$Q_7$ is the same as $Q_4$;
X is hydroxy, benzyloxy, alkoxy having from 1 to 18 carbon atoms or OM where M is an alkali metal cation, an ammonium cation or a mono-, di- or trialkylammonium cation having from 1 to 18 carbon atoms;
$Y_1$, $Y_2$, $Y_3$ and $Y_4$ are the same or different and are selected from the group consisting of hydrogen, halo, hydroxyl, lower-alkoxy, alkyl having from 1 to 9 carbon atoms, phenyl-lower-alkyl, $COOR_4$ and $NR_5R_6$ where $R_4$ and $R_5$ are hydrogen or lower alkyl and $R_6$ is hydrogen, lower alkyl, cycloalkyl having from 5 to 7 carbon atoms, lower alkanoyl, phenylsulfonyl or lower-alkyl-substituted phenylsulfonyl;

Z is selected from the group consisting of 9-julolidinyl and a radical having the formula

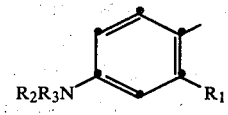

in which:
$R_1$ is selected from the group consisting of hydrogen, halo, lower-alkyl, lower-alkoxy and di-lower-alkylamino;
$R_2$ is lower-alkyl; and
$R_3$ is selected from the group consisting of lower-alkyl, benzyl, phenyl, and phenyl substituted with a lower-alkyl or lower-alkoxy group.

The compounds are useful as color formers in pressure-sensitive carbonless duplicating systems and in thermal-marking systems.

A particular embodiment sought to be patented resides in a compound having Formula II

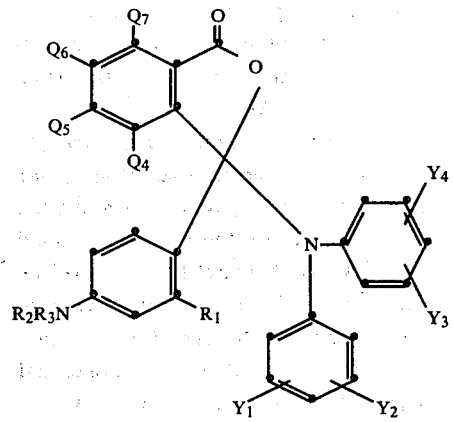

Formula II wherein $R_1$, $R_2$, $R_3$, $Q_4$, $Q_5$, $Q_6$, $Q_7$, $Y_1$, $Y_2$, $Y_3$ and $Y_4$ have the previously given meanings. Preferred compounds within the ambit of this particular embodiment are those wherein:

(a) $Q_4$, $Q_5$, $Q_6$ and $Q_7$ are each hydrogen;
(b) $Q_4$, $Q_5$ and $Q_7$ are each hydrogen and Q is di-lower-alkylamino; and
(c) $Q_4$, $Q_5$, $Q_6$ and $Q_7$ are each halo, especially: 3-[4-(dimethylamino)phenyl]-3-[(4-ethoxyphenyl)-phenylamino]-phthalide; 3-[4-(dimethylamino)-phenyl]-3-[(4-(isopropoxyphenyl)-phenylamino]phthalide; 4,5,6,7-tetrachloro-3-[4-(dimethylamino)phenyl]-3-[(4-ethoxyphenyl)-phenylamino]phthalide; 3-[4-(diethylamino)-2-methylphenyl]3-[(4-ethoxyphenyl)phenylamino]-phthalide; 3-[4-(dimethylamino)phenyl]-3-[bis(4-octylphenyl)-amino]phthalide; 6-(dimethylamino)-3-[4-(dimethylamino)phenyl]-3-[(4-ethoxyphenyl)-phenylamino]phthalide; 3-[4-(dimethylamino)-phenyl]-3-(diphenylamino)phthalide; 6-(dimethylamino)-3-[4-dimethylamino)phenyl]-3-[bis(4- octylphenyl)amino]phthalide; 3-[4-(ethylbenzylamino)phenyl]-3-[(4-ethoxyphenyl)-phenylamino]phthalide and 3-[4-(diethylamino)-2-methylphenyl]-3-{bis[4-(dimethylamino)phenyl-]amino}phthalide.

In one of its process aspects the invention sought to be patented resides in the process which comprises reacting a 2-substituted benzoic acid having Formula III

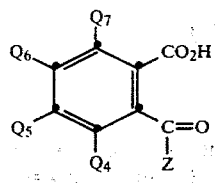

Formula III with a diarylamine having Formula IV

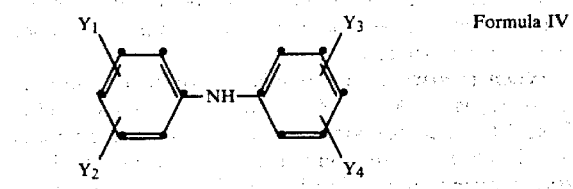

Formula IV in the presence of the anhydride of an alkanoic acid having from 2 to 5 carbon atoms, and an organic base; where in Formulas III and IV, Z, $Q_4$, $Q_7$, $Y_1$, $Y_2$, $Y_3$ and $Y_4$ have the previously given meanings; $Q_5$ is the same as $Q_4$; or di-lower-alkylamino, halo or COX when $Q_4$, $Q_6$ and $Q_7$ are hydrogen; $Q_6$ is the same as $Q_4$; or di-lower-alkylamino, halo or COX when $Q_4$, $Q_5$ and $Q_7$ are hydrogen; and X is hydroxy, benzyloxy or alkoxy having from 1 to 18 carbon atoms.

In another process aspect the invention sought to be patented resides in the process which comprises reacting a 2-substituted benzoic acid of Formula III with an inorganic acid chloride selected from the group consisting of thionyl chloride, phosphorus oxychloride, phosphorus trichloride and phosphorus pentachloride followed by reaction of the resulting product with a diarylamine of Formula IV in the presence of an organic base; where in Formulas III and IV, Z, $Q_4$, $Q_5$, $Q_6$, $Q_7$, $Y_1$, $Y_2$, $Y_3$ and $Y_4$ have the meanings given in the preceding paragraph.

In an article-of-manufacture aspect the invention sought to be patented resides in a pressure-sensitive carbonless duplicating system or thermal marking system containing a color-forming substance comprising a compound having Formula I.

A particular embodiment sought to be patented resides in a pressure-sensitive transfer sheet, adapted for use with a receiving sheet having an electron accepting layer, comprising a support sheet coated on one side with a layer of pressure-rupturable microcapsules, said microcapsules containing a liquid solution of a color forming substance comprising at least one compound having Formula I.

Another particular embodiment sought to be patented resides in a heat responsive record material comprising a support sheet coated on one side with a layer containing a mixture comprising at least one color-forming compound having Formula I and an acidic developer arranged such that application of heat will produce a mark-forming reaction between the color-forming compound and the acidic developer.

Preferred articles within the ambit of the particular embodiments above-described are those wherein the color-forming component comprises a compound having Formula II, especially where in Formula II:

(a) $Q_4$, $Q_5$, $Q_6$ and $Q_7$ are each hydrogen;
(b) $Q_4$, $Q_5$ and $Q_7$ are each hydrogen and $Q_6$ is di-lower-alkylamino, and
(c) $Q_4$, $Q_5$, $Q_6$ and $Q_7$ are each halo.

As used herein the term "halo" includes chloro, fluoro, bromo and iodo. Chloro is the preferred hal substituent because of the relatively low cost and ease of preparation of the required chloro-substituted intermediates and because the other halogens offer no particular advantages over chloro. However the other above-named halo substituents are also satisfactory.

The terms "lower-alkyl", lower-alkoxy and di-lower-alkylamino" denote saturated, acyclic groups having from 1 to 4 carbon atoms which may be straight or branched as exemplified by methyl, ethyl, propyl, isopropyl, butyl, sec-butyl, isobutyl, tert-butyl, methoxy, ethoxy, propoxy, isopropoxy, butoxy, sec-butoxy, isobutoxy, tert-butoxy, dimethylamino, diethylamino, ethylmethylamino, dipropylamino, dibutylamino, isobutylmethylamino, di-tert-butylamino and the like.

As used herein the term "alkyl of one to nine carbon atoms" denotes saturated monovalent straight or branched chain aliphatic hydrocarbon radicals including methyl, ethyl, propyl, isopropyl, butyl, isobutyl, tert-butyl, amyl, 1-methylbutyl, 3-methylbutyl, hexyl, isohexyl, heptyl, isoheptyl, octyl, isooctyl, 2-ethylhexyl, nonyl, 3-ethylheptyl and the like.

As used herein the term "cycloalkyl having from 5 to 7 carbon atoms" includes cyclopentyl, cyclohexyl and cycloheptyl.

The term "lower alkanoyl" denotes saturated acyclic acyl groups having from 1 to 5 carbon atoms which may be straight or branched as exemplified by formyl, acetyl propionyl, butyryl, isobutyryl, valeryl, 2-methylbutyryl, isovaleryl, pivalyl and the like.

The term "phenyl-lower-alkyl includes benzyl, 2-phenylethyl, 2-phenylpropyl, 3-phenylpropyl, 1-phenylbutyl, 2,2-dimethyl-2-phenylethyl and the like. If desired the phenyl group may contain a lower alkyl or lower alkoxy substituent.

The term "alkoxy having from 1 to 18 carbon atoms" includes, in addition to the above-noted lower-alkoxy groups, saturated, acyclic, straight or branched-chain groups such as n-pentyloxy, n-hexyloxy, n-heptyloxy, n-octyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, n-octadecyloxy, 1-methylpentyloxy, 2,2-dimethylbutyloxy, 2-methylhexyloxy, 1,4-dimethylpentyloxy, 3-ethylpentyloxy, 2-methylheptyloxy, 1-ethylhexyloxy, 2-propylpentyloxy, 2-methyl-3-ethylpentyloxy, 1,3,5-trimethylhexyloxy, 1,5-dimethyl-4-ethylhexyloxy, 5-methyl-2-butylhexyloxy-2-propylnonyloxy, 2-butyloctyloxy, 1,1-dimethylundecyloxy, 2-pentylnonyloxy, 1,2-dimethyltetradecyloxy, 1,1-dimethylpentadecyloxy and the like.

As used herein the term "alkali metal" includes lithium, sodium and potassium.

The term "mono-, di- or tri-alkylammonium cation" includes ammonium cations substituted by from 1 to 3 alkyl groups as above described. The alkyl groups can be the same or different provided the ammonium cation contains no more than 18 carbon atoms. As examples there can be named methylammonium, t-butylammonium, t-octylammonium, n-dodecylammonium, n-octadecylammonium, di-n-butylammonium, di-n-nonylammonium, isopropyl-n-butylammonium, dimethyl-n-butylammonium, triethylammonium, N-ethyl-N,N-diisopropylammonium, tributylammonium, di-n-butyl-n-octylammonium and the like.

The term "9-julolidinyl" of course refers to the radical having Formula V

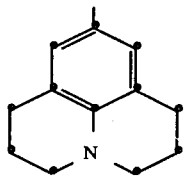

Formula V

Anhydrides of alkanoic acids of two to five carbon atoms include acetic anhydride, propionic anhydride, butyric anhydride, isobutyric anhydride, valeric anhydride, isovaleric anhydride, α-methylbutyric anhydride, pivalic anhydride and the like. Acetic anhydride is preferred because of its low cost and high reactivity, however the other above-named anhydrides are also satisfactory.

Organic bases include pyridine, collidine, tri-lower-alkyl amines, urea, diarylamines of Formula IV hereinabove and the like. Because of their low cost and ready availability pyridine and urea are preferred.

In accordance with one of the process aspects of this invention the compounds having Formula I are obtained by reacting approximately equimolar amounts of a 2-substituted benzoic acid of Formula III and a diarylamine of Formula IV in the anhydride of an alkanoic acid having from two to five carbon atoms, such as acetic anhydride, with or without an inert diluent and in the presence of an organic base, for example pyridine or urea, at a temperature of from 0° to 100° C. for from approximately 10 minutes to 24 hours. The reaction is usually carried out in the absence of an inert diluent at about 20° to 40° C. for approximately 0.5 to 2 hours. If desired an excess of the diarylamine reactant can be employed as the organic base. The product thus obtained can be isolated by filtration if it is insoluble in the reaction medium or by dilution of the reaction medium with a miscible solvent in which the product is insoluble such as a lower-alkanol or low molecular weight hydrocarbon for example isopropyl alcohol or hexane or a mixture of these in order to effect precipitation of the product. Alternatively, the reaction mixture can be poured into aqueous base such as dilute ammonium hydroxide, sodium hydroxide, sodium carbonate or sodium bicarbonate and the product extracted with an organic solvent such as benzene or toluene followed by evaporation of the organic solvent leaving the product as a residue. The product once isolated can be purified by conventional means such as trituration or recrystallization from a suitable solvent.

In accordance with a second process aspect of the invention the compounds of Formula I can be prepared in two steps which comprise first reacting a 2-substituted benzoic acid of Formula III with an excess of an inorganic acid chloride such as thionyl chloride, phosphorus oxychloride, phosphorus trichloride or phosphorus pentachloride with or without an inert diluent such as benzene, toluene, chloroform or 1,2-dichloroethane, at 20° to 80° C. for about 0.5 to 2 hours; and following removal of excess inorganic acid chloride, reaction of the resulting product which while not having been isolated is presumed to be a halide having Formula VI

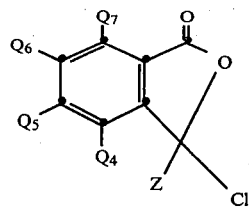

Formula VI in which $Q_4$, $Q_5$, $Q_6$, $Q_7$ and Z have the meanings previously given in Formula III, with a diarylamine of Formula IV hereinabove in an inert solvent in the presence of an organic base as previously described at a temperature in the range of 0° to 80° C. for about 1 to 48 hours. The product can be isolated and purified in the manner previously described.

When preparing compounds of Formula I wherein $Q_5$ or $Q_6$ is COX and X is benzyloxy, alkoxy having from 1 to 18 carbon atoms or OM where M is an alkali metal cation, an ammonium cation or a mono, di or trialkylammonium cation having from 1 to 18 carbon atoms it is ordinarily preferred to first prepare the compound of Formula I wherein $Q_5$ or $Q_6$ is COOH followed by conversion of the carboxyl group to the desired ester, alkali metal salt or ammonium salt in accordance with conventional procedures.

The 2-substituted benzoic acids of Formula III required as starting materials in the preparation of the products of Formula I are generally known or if specifically new can be prepared in accordance with the procedures described for the preparation of the known compounds, for example as disclosed in British Pat. No. 1,435,179, published May 12, 1976, i.e., by reacting a phthalic anhydride having Formula VII Formula VII with julolidine or an appropriate aniline having Formula VIII Formula VIII under Friedel-Crafts conditions, where in Formula VII $Q_4$, $Q_5$, $Q_6$ and $Q_7$ have the meanings given above in Formula III, and in Formula VIII $R_1$, $R_2$ and $R_3$ have the previously given meanings. It will, of course, be appreciated that when $Q_5$ (or $Q_6$) of the phthalic anhydride (Formula VII) is halo, COX or di-lower-alkylamino the reaction can produce isomers or a mixture of isomers, viz. 2-substituted benzoic acids of Formula III having a halo, COX or di-lower-alkylamino substituent at the 4-position ($Q_5$) or the 5-position ($Q_6$) or a mixture of these. In the latter instance the isomeric 2-substituted benzoic acids can be separated by conventional means such as fractional crystallization or chromatography. Alternatively, the mixture of 2-substituted benzoic acids can be reacted with a diarylamine of Formula IV to produce a mixture of 5 and 6- substituted phthalides of Formula I which, if desired, can be separated or simply used as the mixture in the practice of this invention.

The diarylamines of Formula IV which are also required as starting materials in the processes of the invention belong to a well known class of compounds and are either commercially available or readily obtained by conventional procedures well known in the art.

The novel compounds of Formula I hereinabove are essentially colorless in the depicted form. When contacted with an acidic medium, for example silica gel or one of the types ordinarily employed in pressure-sensitive carbonless duplicating systems such as silton clay or phenolic resins the compounds of Formula I develop a yellow to black colored image of good to excellent tinctorial strength, and possessing excellent light stability, resistance to sublimation and xerographic copiability. The compounds are thus highly suitable for use as colorless precursors, that is color-forming substances in pressure-sensitive carbonless duplicating systems. The compounds which produce a yellow to red color can be used as toners in admixture with other color formers to produce images of a neutral shade which desirably are readily copiable by xerographic means. The compounds of Formula I wherein at least one of $Y_1$ and $Y_2$ and at least one of $Y_3$ and $Y_4$ are simultaneously di-lower-alkylamino develop a purple to black image when contacted with an acidic medium and are accordingly of particular value as color precursors. Moreover, the compounds of Formula I, in particular whose wherein $Q_5$ or $Q_6$ is COX and X is alkoxy having from 1 to 18 carbon atoms, or those wherein one or more of $Y_1$, $Y_2$, $Y_3$ and $Y_4$ are alkyl of 1 to 9 carbon atoms, have enhanced solubility in common and inexpensive organic solvents such as odorless mineral spirits, kerosene, vegetable oils and the like; and those wherein $Q_5$ or $Q_6$ is COX and X is OM in which M has the previously given meaning are soluable in water and lower-alkanols thereby avoiding the need for more expensive, specialized solvents such as polyhalogenated or alkylated biphenyls which have ordinarily been used to prepare microencapsulated solutions of the color formers of the prior art.

The compounds of this invention may be incorporated in any of the commercially accepted systems known in the carbonless duplicating art. A typical technique for such application is as follows. Solutions containing one or more colorless precursor compounds of Formula I, optionally in admixture with other color formers, in suitable solvents are microencapsulated by well-known procedures for example as described in U.S. Pat. No. 3,649,649. The microcapsules are coated on the reverse side of a transfer sheet with the aid of a suitable binder and the coated transfer sheet is then assembled in a manifold with the microcapsule coated side in contact with a receiving sheet coated with an electron accepting substance, for example, silton clay or a phenolic resin. Application of pressure to the manifold such as that exerted by a stylus, typewriter or other form of writing or printing causes the capsules on the reverse side to rupture. The solution of the color former released from the ruptured microcapsules flows to the receiving sheet and on contact with the acidic medium thereon forms a yellow to red colored image of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formula I are intimately mixed with an acidic developer of the type generally employed in thermal papers such as described in U.S. Pat. No. 3,539,375, that is, papers which produce a colored image when contacted with a heated stylus or heated type, for example, bisphenol A. heating of the mixture produces a colored image of varying shades from yellow to purple depending on the particular compound of the invention employed. The ability of the compounds of Formula I to form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art.

The compounds of this invention which are soluble in water and lower-alkanols may be incorporated in any of the commercial hectographic or spirit-reproducing copying systems such as described in British Pat. No. 1,427,318 published Mar. 10, 1976. In such systems a transfer sheet coated on one side with a layer containing one or more water- or lower alkanol-soluble color formers of Formula I is placed with its coated surface against one surface of a master paper which is then typed, written or marked on, causing transfer of the coating as a substantially colorless reverse image to the master paper at the points where the transfer sheet and master paper have been pressed together. The master paper is then brought into contact with a succession of sheets of paper moistened with a suitable spirit-reproducing fluid such as ethanol.

The molecular structures of the compounds of this invention were assigned on the basis of the modes of synthesis, elemental analysis and study of their infrared, nuclear magnetic resonance, and mass spectra.

The following examples will further illustrate the invention without, however, limiting it thereto.

EXAMPLE 1

A mixture containing 5.4 g. of 2-[4-(dimethylamino)-benzoyl]benzoic acid, 3.4 g. of diphenylamine, 2 ml. of pyridine and 15 ml. of acetic anhydride was stirred at room temperature. After a few minutes the solid reactants were completely dissolved and after 15 minutes an orange solid precipitated. The reaction mixture was stirred an additional 15 minutes and then diluted with 20 ml. of 2-propanol and 50 ml. of ligroin. After stirring an additional 10 minutes the solids were collected, washed with ligroin and 2-propanol (which removed an orange impurity) and dried to give 5.9 g. of 3-[4-(dimethylamino)phenyl]-3-(diphenylamino)phthalide as a cream solid, m.p. 188°–190° C. (dec.). A toluene solution of the product contacted with acidic clay or phenolic resin developed an orange colored image.

EXAMPLE 2

A mixture containing 5.4 g. of 2-[4-(dimethylamino)-benzoyl]benzoic acid, 4.3 g. of 4-ethoxy-N-phenylaniline, 0.5 g. of urea and 15 ml. of acetic anhydride was stirred 0.5 hr. at room temperature. Complete dissolution of the solid reactants was followed shortly by precipitation of the product. After diluting the reaction mixture with 20 ml. of 2-propanol the product was collected, washed with 2-propanol and dried to give 8.4 g. of 3-[4-(dimethylamino)phenyl]-3-[(4-ethoxyphenyl)phenylamino]phthalide as a white solid, m.p. 214°–216° C. (dec.). A toluene solution of the product contacted with acidic clay or phenolic resin developed an orange colored image.

EXAMPLE 3

A mixture containing 6.24 g. (0.02 mole) of 5-(dimethylamino)-2-[4-(dimethylamino)benzoyl]benzoic acid, 6.25 g. (0.03 mole) of 4-ethoxy-N-phenylaniline and 20 ml. of acetic anhydride was stirred at room temperature for 20 hours. The reaction mixture was then diluted with 30 ml. of 2-propanol and stirred an additional 0.5 hr. The solids were collected, washed with ligroin and dried to give 9.3 g. of 6-(dimethylamino)-3-[4-(dimethylamino)phenyl]-3-[(4-ethoxyphenyl)-phenylamino]phthalide as a pale pink solid, m.p. 200°–202° C. (dec.). A toluene solution of the product contacted with acidic clay or phenolic resin developed an orange colored image, which, on acidic clay, became green after exposure to fluoroecent light

EXAMPLE 4

A mixture containing 2.0 g. of 2[2,4-bis(dimethylamino)benzoyl]benzoic acid, 1.4 g. of 4-ethoxy-N-phenylaniline, 1 ml. of pyridine and 8 ml. of acetic anhydride was stirred 1.5 hrs. at room temperature. Dilution with 20 ml. of 2-propanol and 50 ml. of ligroin produced no precipitate. The reaction mixture was therefore poured into 10% aqueous ammonia and the product was extracted with toluene. The organic extracts were washed with water and saturated aqueous sodium chloride and evaporated to dryness under vacuum. Trituration of the residue with ligroin afforded 2.18 g. of 3-[2,4-bis-(dimethylamino)phenyl]-3-[(4-ethoxyphenyl)-phenylamino]-phthalide as a pale orange solid, m.p. 111°–117° C. (dec.). A toluene solution of the product contacted with acidic clay or phenolic resin developed an orange colored image.

EXAMPLE 5

A mixture containing 1.7 g. of 3,4,5,6-tetrachloro-2-[4-(dimethylamino)benzoyl]benzoic acid, 0.5 ml. of thionyl chloride and 200 ml. 1,2-dichloroethane was heated 0.5 hr. under reflux to produce a pale green solution. After cooling to 35° C. a solution containing 1.0 g. of 4-ethoxy-N-phenylaniline and a few drops of pyridine in 10 ml. of 1,2-dichloroethane was added and stirring at room temperature was continued for 2 days. The reaction mixture was then poured into 10% aqueous ammonia and the product extracted with 1,2-dichloroethane. The organic extracts were washed with water and saturated aqueous sodium chloride and evaporated to dryness under vacuum. The residue was slurried in 100 ml. of acetone and a white water-soluble solid was filtered off. The filtrate was evaporated to dryness and the residue was triturated with 2-propanol to give 1.5 g. of crude 4,5,6,7- tetrachloro-3-[4-(dimethylamino)phenyl]-3-[(4-ethoxyphenyl)- phenylamino]phthalide as a gray solid, m.p. 112°–121° C. The nmr spectrum indicated the product to be a mixture containing the desired phthalide and unreacted 3,4,5,6-tetrachloro-2-[4-(dimethylamino)benzoyl]benzoic acid in an approximate ratio of 60:40. A toluene solution of the product contacted with acidic clay developed a brown colored image; and when contacted with phenolic resin produced a pinkish-purple colored image.

EXAMPLE 6

Following a procedure similar to that described in Example 1 but employing 6.24 g. of 5-(dimethylamino)-2-[4-(dimethylamino)benozoyl]benzoic acid and 3.4 g. of diphenylamine there was obtained 8.67 g. 6-(dimethylamino)-3-[4-(dimethylamino)phenyl]-3-(diphenylamino)phthalide, m.p. 159°–160° C. A toluene solution of the product contacted with acidic clay or phenolic resin developed a red color image which, on acidic clay, became green after exposure to fluoroescent light.

EXAMPLE 7

Following a procedure similar to that described in Example 1 but employing 3.1 g. of 2-[4-(diethylamino)-2-methylbenzoyl]benzoic acid and 2.1 g. of 4-ethoxy-N-phenylaniline there was obtained 3.7 g. of 3-[4-(diethylamino)-2-methylphenyl]-3-[(4-ethoxyphenyl)-phenylamino]phthalide, m.p. 176°–178° C. (dec.). A toluene solution of the product contacted with acidic clay or phenolic resin developed a red colored image.

EXAMPLE 8

Following a procedure similar to that described in Example 1 but employing 2.7 g. of 2-[4-(dimethylamino)benzoyl]-benzoic acid and 1.9 g. of 3-methyl-N-phenylaniline there was obtained 2.7 g. of 3-[4-(dimethylamino)phenyl]-3-[(3-methylphenyl)-phenylamino]phthalide, m.p. 185°–187° C. A toluene solution of the product contacted with acidic clay or phenolic resin developed an orange colored image.

EXAMPLE 9

Following a procedure similar to that described in Example 1 but employing 2.7 g. of 2-[4-(dimethylamino)benzoyl]-benzoic acid and 2.5 g. of 4-isopropoxy-N-phenylaniline there was obtained 4.34 g. of 3-[4-(dimethylamino)phenyl]-3-[(4-isopropoxyphenyl)-phenylamino]phthalide, m.p. 181°–184° C. A toluene solution of the product contacted with acidic clay or phenolic resin developed an orange colored image.

EXAMPLE 10

Following a procedure similar to that described in Example 1 but employing 3.1 g. 2-[4-(diethylamino)-2-methyl)-benzoyl]benzoic acid and 2.5 g. of 4-isopropoxy-N-phenylaniline there was obtained 3.9 g. of 3-[4-(diethylamino)-2-methylphenyl]-3[(4-isopropoxyphenyl)phenylamino]phthalide, m.p. 176°–178° C. A toluene solution of the product contacted with acidic clay or phenolic resin developed a red colored image.

EXAMPLE 11

Following a procedure similar to that described in Example 1 but employing 3.61 g. of 2[4-(N-p-anisoyl-N-methylamino)benzoyl]benzoic acid (m.p. 235°–242° C.) and 2.13 g. of 4-ethoxy-N-phenylaniline there was obtained 1.88 g. of 3-[4-(N-p-anisoyl-N-methylamino)- phenyl]-3-[(4-ethoxyphenyl)phenylamino]phthalide, m.p. 63°–68° C. (dec.). A toluene solution of the product contacted with acidic clay or phenolic resin developed an orange colored image.

EXAMPLE 12

Following a procedure similar to that described in Example 1 but employing 3.21 g. of 2-(9-julolidinylcarbonyl)-benzoic acid and 2.13 g. of 4-ethoxy-N-phenylaniline there was obtained 4.61 g. of 3-(9-julolidinyl)-3-[(4-ethoxyphenyl)phenylamino]phthalide, m.p. 143°–147° C. A toluene solution of the product contacted with acidic clay or phenolic resin developed a red colored image.

EXAMPLE 13

Following a procedure similar to that described in Example 4 but employing 5.4 g. of 2-[4-(dimethylamino)benzoyl]-benzoic acid and 4.0 g. of 4-hydroxy-N-phenylaniline there was obtained 5.6 g. of 3-[4-dimethylamino)phenyl]-3-[(4-hydroxyphenyl)-phenylamino]phthalide, m.p. 81°–95° C. (dec.). A toluene solution of the product contacted with acidic clay or phenolic resin developed an orange colored image.

EXAMPLE 14

Following a procedure similar to that described in Example 4 but employing 1.4 g. of 2-[4-(diethylamino)-2-methylbenzoyl]benzoic acid and 0.9 g. of diphenylamine there was obtained 1.36 g. of 3-[4-(diethylamino)-2-methylphenyl]-3-(diphenylamino)-phthalide, m.p. 173°–175° C. (dec.). A toluene solution of the product contacted with acidic clay or phenolic resin developed a red colored image.

EXAMPLE 15

Following a procedure similar to that described in Example 4 but employing 3.1 g. of 2-[4-(diethylamino)-2-methylbenzoyl]benzoic acid and 2.1 g. of 3-methyl-N-phenylaniline there was obtained 1.2 g. of 3-[4-(diethylamino)-2-methylphenyl]-3-[(3-methylphenyl)-phenylamino]phthalide, m.p. 155°–156° C. A toluene solution of the product contacted with acidic clay or phenolic resin developed a red colored image.

EXAMPLE 16

Following a procedure similar to that described in Example 4 but employing 1.0 g. of 2-[4-(dimethylamino)-benzoyl]-benzoic acid and 1.4 g. of 4,4'-dioctyldiphenylamine there was obtained 0.62 of 3-[4-(dimethylamino)phenyl]-3-[bis(4-octylphenyl)-amino]phthalide, m.p. 158°–169° C. A toluene solution of the product contacted with acidic clay or phenolic resin developed an orange colored image. In another preparation carried out in a manner similar to that described in Example 2 the product was obtained as a solid, m.p. 163°–167° C.

A 2 percent (W/V) toluene solution of the product of this example was mixed in varying proportions with a 2 percent (W/V) toluene solution of the known color former crystal violet lactone (CVL) and the resulting solution was contacted with phenolic resin with the following results.

| Cpd. of Ex. 16 (2% solution) | CVL (2% solution) | color of image produced |
| --- | --- | --- |
| 7.0 ml. | 3.0 ml. | brownish violet black |
| 6.5 ml. | 3.5 ml. | brownish violet black |
| 6.0 ml. | 4.0 ml. | violet black |
| 5.0 ml. | 5.0 ml. | bluish black |

EXAMPLE 17

Following a procedure similar to that described in Example 4 but employing 3.1 g. of 2-[4-(diethylamino)-2-methylbenzoyl]benzoic acid and 4.0 g. of 4,4'-dioctyldiphenylamine there was obtained 0.41 g. of 3-[4-(diethylamino)-2-methylphenyl]-3-[bis(4-octylphenyl)amino]phthalide, m.p. 85°–110° C. A toluene solution of the product contacted with acidic clay or phenolic resin developed a red colored image. Another preparation carried out in a manner similar to that described in Example 1 afforded a product m.p. 176°–179° C.

EXAMPLE 18

Following a procedure similar to that described in Example 4 but employing 2.7 g. of 2-[4-(diethylamino)-benzoyl]benzoic acid and 5 g. of 3,3'-diethyl-5,5'-dinonyldiphenylamine there was obtained crude 3-[4-(dimethylamino)phenyl]-3-[bis (3-ethyl-5-nonylphenyl)amino]phthalide as a gum. A toluene solution of the product contacted with acidic clay or phenolic resin developed a yellow colored image.

EXAMPLE 19

Following a procedure similar to that described in Example 4 but employing 6.1 g. of 2-[2-chloro-4-(dimethylamino)benzoyl] benzoic acid and 4.2 g. of 4-ethoxy-N-phenylaniline there was obtained crude 3-[2-chloro-4-(dimethylamino)-phenyl]-3-[(4-ethoxyphenyl)-phenylamino]phthalide as a gum. A toluene solution of the product contacted with acidic clay or phenolic resin developed a red colored image.

EXAMPLE 20

Following a procedure similar to that described in Example 4 but employing 2.7 g. of 2-[4-(dimethylamino)benzoyl]benzoic acid and 2.1 g. of 3-chloro-N-phenylamiline there was obtained 1.6 g. of 3-[4-(dimethylamino)phenyl]-3-[(3-chlorophenyl)-phenylamino]- phthalide, m.p. 128°–138° C. A toluene solution of the product contacted with acidic clay or phenolic resin developed an orange colored image.

EXAMPLE 21

Following a procedure similar to that described in Example 1 but employing 2.6 g of 2-[4-(dimethylamino)benzoyl]-benzoic acid and 2.1 g of 4-(dimethylamino)-N-phenylaniline there was obtained 2.2 g of 3-[4-(dimethylamino)phenyl]-3-{[4-(dimethylamino)-phenylamino}phthalide, m.p. 163°–166° C. A toluene solution of the product contacted with acidic clay or phenolic resin developed a brown-colored image.

EXAMPLE 22

Following a procedure similar to that described in Example 1 but employing 3.1 g. of 5-(dimethylamino)-2-[4-(dimethylamino)benzoyl]benzoic acid and 3.0 g of 4-(dimethylamino)-N-phenylaniline there was obtained 3.8 g of 6-(dimethylamino)-3-[4-dimethylamino)-phenyl]-3-{[4-(dimethylamino)phenyl]- phenylamino}phthalide, m.p. 163°–164° C. A toluene solution of the product contacted with acidic clay or phenolic resin developed a brown-colored image which changed to green on clay after fluorescent light exposure.

EXAMPLE 23

Following a procedure similar to that described in Example 1 but employing 4.0 g of 2-[4-(diethylamino)-2-methyl)benzoyl]benzoic acid and 4.0 g of 4-(dimethylamino)-N-phenylaniline there was obtained 3-[4-diethylamino)-2-methylphenyl]-3-{[14-(dimethylamino)phenyl]phenylamino}phthalide, m.p. 154°–156° C. A toluene solution of the product contacted with acidic clay or phenolic resin developed a dark grape-colored image.

EXAMPLE 24

Following a procedure similar to that described in Example 4 but employing 2.6 g of 2-[4-(dimethylamino)benzoyl]- benzoic acid and 2.3 g of methyl 2-anilinobenzoate there was obtained 1.3 g of 3-[4-(dimethylamino)phenyl]-3-{[2-(methoxycarbonyl)phenyl phenylamino}phthalide, m.p. 92.5°–102° C. A toluene solution of the product contacted with acidic clay developed a yellow-colored image.

EXAMPLE 25

Following a procedure similar to that described in Example 4 but employing 3.1 g of 2-[4-(diethylamino)-2-methyl)-benzoly]benzoic acid and 2.3 g of methyl 2-anilinobenzoate there was obtained 1.4 g of 3-[4-(diethylamino)-2-methylphenyl]-3-{[2-(methoxycarbonyl)-phenyl]phenylamino}phthalide, m.p. 51°–126° C. A toluene solution of the product contacted with acidic clay or phenolic resin developed an orange-colored image.

EXAMPLE 26

Following a procedure similar to that described in Example 4 employing 5.2 g of 2-[4-(dimethylamino)-benzoyl[ benzoic acid and 7.0 g of 4,4'-bis-(dimethylamino)diphenylamine there was obtained 10.7 g of 3-[4-(dimethylamino)phenyl]-3-{bis[4-(dimethylamino)-phenyl]amino}phthalide, m.p. 67°–143° C. A toluene solution of the product contacted with acidic clay or phenolic resin developed a brown-colored image.

EXAMPLE 27

Following a procedure similar to that described in Example 1 but employing 4.0 g of 2-[4-(dimethylamino)benzoyl]benzoic acid and 3.4 g of 4-acetamido-N-phenylaniline there was obtained 5.9 g. of 3-[4-(dimethylamino)phenyl]-3-[N-(4-acetamidophenyl)phenylamin]phthalide, m.p. 182°–184.5° C. An acetone solution of the product contacted with acidic clay or phenolic resin developed an orange-colored image.

Example 28

Following a procedure similar to that described in Example 1 but employing 4.6 g of 2-[4-(diethylamino)-2-methyl)benzoyl]benzoic acid and 3.4 g of 4-acetamido-N-phenylaniline there was obtained 5.6 g of 3-[4-(diethylamino)-2-methylphenyl]-3-[(4-acetamidophenyl)phenylamino]phthalide, m.p. 169°–171° C. An acetone solution of the product contacted with acidic clay or phenolic resin developed a red-colored image.

EXAMPLE 29

Following a procedure similar to that described in Example 4 but employing 3.2 g of 2-[4-(diethylamino)-2-methyl)benzoyl]benzoic acid and 2.9 g of 4,4'-diacetamidodiphenylamine there was obtained 0.82 g of 3-[4-(diethylamino)-2-methylphenyl]-3-[bis(4-acetamidophenyl)amino]phthalide, m.p. 179°–182° C. An acetone solution of the product contacted with acidic clay or phenolic resin developed a red-colored image.

EXAMPLE 30

Following a procedure similar to that described in Example 4 but employing 4.0 g of 5-(dimethylamino)-2-[4-(ethylbenzylamino)benzoyl]benzoic acid and 2.2 g of 4-ethoxy-N-phenyl aniline there was obtained 3.0 g of 6-(dimethylamino)-3-[4-(ethylbenzylamino)phenyl]-3-[(4-ethoxyphenyl)phenylamino]phthalide, m.p. 148°–152° C. A toluene solution of the product contacted with acidic clay or phenolic resin developed an orange-colored image which changed to green on clay after fluorescent light exposure.

EXAMPLE 31

Following a procedure similar to that described in Example 2 but employing 5.4 g of 2-[4-(ethylbenzylamino)benzoyl]-benzoic acid and 3.1 g of 4-ethoxy-N-phenylaniline there was obtained 7.5 g of 3-[4-(ethylbenzylamino)phenyl]-3-[(4-ethoxy-phenyl)-phenylamino]phthalide, m.p. 163°–173° C. A toluene solution of the product contacted with acidic clay or phenolic resin developed an orange-colored image.

EXAMPLE 32

Following a procedure similar to that described in Example 3 but employing 3.2 g of 2-[4-(diethylamino)-2-methyl)-benzoyl]benzoic acid and 5 g of 4-octyl-4'-arylalkyldiphenylamine which is available from the B. F. Goodrich Chemical Company under the trade name Good-rite Antioxidant 3190 there was obtained 3-[4-(diethylamino)-2-methylphenyl]-3-{(4-octylphenyl)[4-(arylalkyl)phenyl]amino}phthalide as an oil. A toluene solution of the product contacted with acidic clay or phenolic resin developed a red-colored image.

EXAMPLE 33

Following a procedure similar to that described in Example 1 but employing 15.6 g of 5-(dimethylamino)-2-[4-(dimethylamino)benzoyl]benzoic acid and 19.6 g of 4,4'-dioctyldiphenylamine there was obtained 30.0 g of 6-(dimethylamino)-3-[4-(dimethylamino)phenyl]-3-[bis(4-octylphenyl)amino]phthalide, m.p. 208°–210° C. A toluene solution of the product contacted with acidic clay or phenolic resin developed an orange-colored image which changed to green on the clay after fluoroescent light exposure.

EXAMPLE 34

Following a procedure similar to that described in Example 4 but employing 3.4 g of 2-[4-(diethylamino)-2-ethoxy)benzoyl]benzoic acid and 4.0 g of 4,4'-dioctyldiphenylamine there was obtained 3-[4-(diethylamino)-2-ethoxyphenyl]-3-[bis-(4-octylphenyl)amino]phthalide as an oil. A toluene solution of the product contacted with acidic clay or phenolic resin developed an orange-colored image.

EXAMPLE 35

Following a procedure similar to that described in Example 4 but employing 5.1 g of 2-[4-(diethylamino)-2-ethoxy)-benzoyl]benzoic acid and 3.4 g of 4-acetamido-N-phenylaniline there was obtained 4.8 g of 3-[4-(diethylamino)-2-ethoxyphenyl]-3-[(4-acetamidophenyl)phenylamino]phthalide, m.p. 126°-131° C. A toluene solution of the product contacted with acidic clay or phenolic resin developed an orange-colored image.

EXAMPLE 36

Following a procedure similar to that described in Example 1 but employing 5.7 g of 2-[4-(dimethylamino)-2-methylbenzoyl]benzoic acid and 8.0 g of 4,4'-dioctyldiphenylamine there was obtained 6.2 g of 3-[4-(dimethylamino)-2-methylphenyl]-3-[bis(4-octylphenyl)amino]phthalide, m.p. 172°-174° C. A toluene solution of the product contacted with acidic clay or phenolic resin developed a red-colored image.

EXAMPLE 37

Following a procedure similar to that described in Example 4 but employing 4.6 g of 2-[4-(diethylamino)-2-methyl)-benzoyl]benzoic acid and 4.5 g of 4,4'-bis-(diethylamino)diphenylamine there was obtained 0.53 g of 3-[4-(diethylamino)-2-methylphenyl]-3-{bis[4-(diethylamino)phenyl]amino}phthalide, m.p. 58°-71° C. A toluene solution of the product contacted with acidic clay or phenolic resin developed a black-colored image.

EXAMPLE 38

Following a procedure similar to that described in Example 4 but employing 4.6 g of 2-[4-(diethylamino)-2-methyl)-benzoyl]benzoic acid and 5.0 g of 4-(diethylamino)-4'-(dimethylamino)diphenylamine there was obtained 5.9 g of 3-[4-(diethylamino)-2-methylphenyl]-3-{[4-(diethylamino)phenyl][4-(dimethylamino)phenyl]amino}phthalide, m.p. 68°-83° C. A toluene solution of the product contacted with acidic clay or phenolic resin developed a black-colored image.

EXAMPLE 39

Following a procedure similar to that described in Example 4 but employing 4.5 g of 2-[4-(dimethylamino)-2-chloro)benzoyl]benzoic acid and 5.0 g of 4-(diethylamino)-4'-(dimethylamino)diphenylamine there was obtained 0.8 g of 3-[4-(dimethylamino)-2-chlorophenyl]-3-{[4-(diethylamino)phenyl][4-(dimethylamino)phenyl]amino}phthalide, m.p. 67°-84° C. A toluene solution of the product contacted with acidic clay or phenolic resin developed a black-colored image.

EXAMPLE 40

Following a procedure similar to that described in Example 4 but employing 5.8 g of 2-[4-(diethylamino)-2-ethoxy)benzoyl]benzoic acid and 3.9 g of 4,4'-bis(-dimethylamino)diphenylamine there was obtained 2.26 g of 3-[4-(diethylamino)-2-ethoxyphenyl]-3-{bis[4-(dimethylamino)phenyl]amino}phthalide, m.p. 58°-69° C. A toluene solution of the product contacted with acidic clay or phenolic resin developed a grapeblack-colored image.

EXAMPLE 41

Following a procedure similar to that described in Example 4 but employing 5.7 g of 2-[4-(dimethylamino)-2-methyl)benzoyl]benzoic acid and 5.0 g of 4,4'-bis(dimethylamino)diphenylamine there was obtained 0.22 g of 3-[4-(dimethylamino)-2-methylphenyl]-3-{bis [4-(dimethylamino)phenyl]amino}phthalide, m.p. 97°-113° C. A toluene solution of the product contacted with acidic clay or phenolic resin developed a black-colored image.

EXAMPLE 42

Following a procedure similar to that described in Example 4 but employing 5.7 g of 2-[4-(dimethylamino)-2-methylbenzoyl]benzoic acid and 5.5 g of 4,4'-bis(diethylamino)diphenylamine there was obtained 1.62 g of 3-[4-(dimethylamino)-2-methylphenyl]-3-{bis[4-(diethylamino)phenyl]amino}phthalide, m.p. 59°-72° C. A toluene solution of the product contacted with acidic clay or phenolic resin developed a black-colored image.

EXAMPLE 43

A.

Following a procedure similar to that described in Example 4 but employing 3.1 g of 2-[4-(diethylamino)-2-methylbenzoyl]benzoic acid and 3.0 g of 4,4'-bis(-dimethylamino)diphenylamine there was obtained 2.95 g of 3-[4-(diethylamino)-2-methylphenyl]-3-{bis[4-(dimethylamino)phenyl]amino}phthalide, m.p. 67°-83° C. A toluene solution of the product contacted with acidic clay or phenolic resin developed a black-colored image.

B.

A mixture containing 6.2 g of 2-[4-(diethylamino)-2-methylbenzoyl]benzoic acid and 5.1 g of 4,4'-bis(dimethylamino)diphenylamine, 20 ml of acetic anhydride and 2.0 g of urea was stirred 2 hours at room temperature and then poured into 5% aqueous ammonium hydroxide and extracted with toluene. The organic extracts were dried over anhydrous sodium sulfate and evaporated to dryness under vacuum. The residue was dissolved in 200 ml of DMF and slowly added to 1 ½ liter of water containing 1 g of Dabco with vigorous stirring. The air dried product was weighed 5.0 g and was essentially identical to the product of part A above.

C.

In a procedure similar to that described in Example 5 was employed, 1.7 g of thionyl chloride was added to a mixture of 100 ml of benzene and 50 ml of 1,2-dichloroethane. After 4.7 g of 2-[4-(diethylamino-2-methylbenzoyl]benzoic acid was added, the reaction mixture was warmed to 60° C. to obtain a clear solution. When the solution had cooled to 40° C., a solution of 3.5 g of 4,4'-bis(dimethylamino)diphenylamine and 1 ml of pyridine in 50 ml 1,2-dichloroethane was added and the mix heated to 60° C. for one hour, cooled and stirred overnight at room temperature. The tary material which separated was filtered, washed and dissolved in dimethylformamide. Addition to an excess of water yielded 4.2 g of a light grape-colored solid which developed a black color on silica gel.

EXAMPLE 44

Following a procedure similar to that described in Example 4 but employing 6.2 g of 5-(dimethylamino)-2-[4-(dimethylamino)benzoyl]benzoic acid and 5.0 g of 4,4'-bis-(dimethylanino)diphenylamine there was obtained 6.6 g of 6-(dimethylamino)-3-[4-(dimethylamino)-phenyl]-3-{bis[4-(dimethylamino)phenyl]amino}-phthalide, m.p. 86°–92° C. A toluene solution of the product contacted with acidic clay or phenolic resin developed a brown-colored image which changed to green on clay after fluorescent light exposure.

EXAMPLE 45

Following a procedure similar to that described in Example 4 but employing 1.4 g of 5-(dimethylamino)-2-[4-(N-ethyl-N-benzylamino)benzoyl]benzoic acid and 0.8 g of 4,4'-bis-(dimethylamino)diphenylamine there was obtained 1.0 g of 6-(dimethylamino)-3-[4-(N-ethyl-N-benzyl)aminophenyl]-3-}bis[4-(dimethylamino)-phenyl]amino}phthalide, m.p. 137°–148° C. A toluene solution of the product contacted with acidic clay or phenolic resin developed a dark brown-colored image which changed to green on clay after fluorescent light exposure.

EXAMPLE 46

A.

To a stirred mixture containing 36 g. of 4-(and 5-) carboxy-2-(4-diethylamino-2-hydroxybenzoyl)benzoic acid (prepared from trimellitic anhydride and 3-(diethylamino)phenol, 60 ml. of diethyl sulfate and 450 ml. of acetone at 35° C. was added dropwise over 2 hours a solution containing 25 g. of potassium hydroxide in 75 ml. of water. When the addition was complete stirring was continued an additional 2 hours. Another 20 g. of potassium hydroxide in 60 ml. of water was added and the mixture was heated under reflux 1 hour. Solvent was then allowed to distill until the internal temperature reached 96° C. The reaction mixture was maintained at 96° C. 0.5 hour then stirred at room temperature overnight, diluted with 100 ml. of water and brought to pH 4.0 with 3N hydrochloric acid. The resulting red precipitate was collected, washed with water and air-dried to give 37 g. of 4-(and 5-) carboxy-2-[4-(diethylamino)-2-ethoxybenzoyl]benzoic acid, m.p. 63°–96° C. which was used without further purification.

B.

A mixture containing 8.0 g. of 4-(and 5-)carboxy-2-[4-(diethylamino)-2-ethoxybenzoyl]benzoic acid, 8.0 g. of 4-(dimethylamino)-4'-(diethylamino)diphenylamine, 25 ml. of acetic anhydride and 2 ml. of pyridine was stirred 2 hours at room temperature. The mixture was poured into toluene and the product extracted with 10% aqueous ammonia. The aqueous alkaline extracts were acidified to pH 5 with 3N hydrochloric acid. The resulting precipitate was collected, washed with water and dried to give 4.8 g of 5-(and 6-)carboxy-3-[4-(diethylamino)-2-ethoxyphenyl]-3-{[4-(dimethylamino)phenyl][4-(diethylamino)phenyl]amino}-phthalide, m.p. 167°–173° C.

C.

To a mixture containing 4.0 g. of the above acid, 4.0 g. of potassium carbonate and 100 ml. of N,N-dimethylformamide was added 4.0 g. of dimethyl sulfate. After stirring for one hour, the reaction mixture was poured into 1 liter of water containing 10 ml. of concentrated ammonium hydroxide. The resulting precipitate was collected, washed with water and dried to give 0.2 g. of 5-(and 6-)methoxycarbonyl-3-[4-(diethylamino)-2-ethoxyphenyl]-3-{[4-(dimethylamino)phenyl][4-(diethylamino)phenyl]amino}phthalide, m.p. 87°–93° C. A toluene solution of the product contacted with acidic clay or phenolic resin developed a brown-black colored image.

EXAMPLE 47

A mixture containing 2.0 g. (0.005 mole) of 4-(and 5-)carboxy-2-[4-(diethylamino)-2-ethoxybenzoyl]benzoic acid, 0.9 g. (0.005 mole) of diphenylamine, 6 ml. of acetic anhydride and 1 ml. of pyridine was stirred 2 hrs. at room temperature. Following the addition of 6 ml. of N,N-dimethylformamide the mixture was poured slowly into 130 ml. of cold water and stirred 0.25 hr. The resulting solid product was collected by filtration, washed with water and dried to give 2.5 g. of 5-(and 6-)carboxy-3-[4-(diethylamino)-2-ethoxyphenyl]-3-(diphenylamino)phthalide, m.p. 117°–125° C. (dec.). The product developed a red image on silica gel, acidic clay and phenolic resin.

EXAMPLE 48

To a stirred mixture containing 2.1 g. of 5-(and 6-)carboxy-3-[4-(diethylamino)-2-ethoxyphenyl]-3-(diphenylamino)phthalide, 1.0 g. of potassium carbonate and 25 ml. of N,N-dimethylformamide at 40° C. was added 1.5 g. of dimethyl sulfate. After stirring 2 hr. at 40° C., the reaction mixture was poured into water and the product extracted with toluene. The toluene extracts were washed with water and saturated aqueous sodium chloride and evaporated to dryness under vacuum to give 1.7 g. of 5-(and 6-)methoxycarbonyl-3-[4-(diethylamino)-2-ethoxyphenyl]-3-(diphenylamino)phthalide as a light-brown oil. The product developed a red image on acidic clay and phenolic resin.

EXAMPLE 49

Following a procedure similar to that described in Example 47 but substituting for diphenylamine 1.33 g. (0.005 mole) of 4,4'-bis(dimethylamino)diphenylamine there was obtained 2.65 g. of 5-(and 6-)carboxy-3-[4-(diethylamino)-2-ethoxyphenyl]-3-{bis[4-(dimethylamino)phenyl]amino}phthalide, m.p. 165°–175° C. The product developed a black image on silica gel or acidic clay and a grape image on phenolic resin.

EXAMPLE 50

Following a procedure similar to that described in Example 48 but employing 2.0 g. of 5-(and 6-)carboxy-3-[4-diethylamino)-2-ethoxyphenyl]-3-{bis[4-(dimethylamino)phenyl]amino}phthalide, 1.0 g. of potassium carbonate, 1.5 ml. of diethyl sulfate and 30 ml. of N,N-dimethylformamide there was obtained 0.5 g. of 5-(and 6-)ethoxycarbonyl-3-[4-(diethylamino)-2-ethoxyphenyl]-3-{bis[4-(dimethylamino)phenyl]amino}phthalide as a brown oil. The product developed a brown-black image on acidic clay and phenolic resin.

EXAMPLE 51

Following a procedure similar to that described in Example 47 but employing 3.9 g. of 4-(and 5-)carboxy-2-[4-(dimethylamino)-2-ethoxybenzoyl]benzoic acid, 4.0 g. of 4,4'-dioctyldiphenylamine and substituting for the pyridine 0.5 g. of urea, there was obtained 5.8 g. of 5-(and 6-)carboxy-3-[4-diethylamino)-2-ethoxyphenyl]-3-[bis(4-octylphenyl)amino]phthalide which softened at 230° C. but did not melt below 300° C.

EXAMPLE 52

Following a procedure similar to that described in Example 48 but employing 5.5 g. of 5-(and 6-)carboxy-3-[4-(diethylamino)-2-ethoxyphenyl]-3-[bis(4-octylphenyl)amino]-phthalide, 3.0 g. of potassium carbonate and 4 ml. of dimethyl sulfate there was obtained 5-(and 6-)methoxycarbonyl-3-[4-(diethylamino)-2-ethoxyphenyl]-3-[bis(4-octylphenyl)amino]phthalide as a light brown oil. The product developed a red image on acidic clay and phenolic resin.

EXAMPLE 53

A.

To a stirred mixture containing 9.6 g. (0.05 mole) of ground trimellitic anhydride and 16.3 g. (0.1 mole) of N,N-diethyl-m-toluidine in 100 ml. of dry chlorobenzene at 5° C. was added 20.0 g. (0.15 mole) of aluminum chloride. After stirring overnight at room temperature the reaction mixture was poured into 300 g. of ice-water and stirred for 1 hr. The precipitated solid was collected, washed with water and dried. The crude product was dissolved in 105 ml. of 5% aqueous sodium hydroxide, stirred 10 min. and filtered to remove insoluble material. The filtrate was cooled to 5° C. and acidified with 10% hydrochloric acid. The resulting product was collected, washed with water and dried to give 6.7 g. of 4-(and 5-)carboxy-2-[4-(diethylamino)-2-methylbenzoyl]benzoic acid, m.p. >300° C.

B.

Following a procedure similar to that described in Example 47 but employing 3.6 g. of 4-(and 5-)carboxy-2-[4-(diethylamino)-2-methylbenzoyl]benzoic acid and 4.0 g. of 4,4'-dioctyldiphenylamine there was obtained 6.8 g. of 5-(and 6-)carboxy-3-[4-(diethylamino)-2-methylphenyl]-3-[bis(4-octylphenyl)amino]phthalide, m.p. 99°-102° C. The product developed a purple-red image on silica gel, acidic clay and phenolic resin.

EXAMPLE 54

Following a procedure similar to that described in Example 48 but employing 6.0 g. of 5-(and 6-)carboxy-3-[4-(diethylamino)-2-methylphenyl]-3-[bis(4-octylphenyl)amino]-phthalide, 3.0 g. of potassium carbonate and 5 ml. of dimethyl sulfate, there was obtained 5-(and 6-)methoxycarbonyl-3-[4-(diethylamino)-2-methylphenyl]-3-[bis(4-octylphenyl)amino]-phthalide which developed a red image on acidic clay and phenolic resin.

EXAMPLE 55

Following a procedure similar to that described in Example 47 but employing 4-(and 5-)carboxy-2-[4-(diethylamino)-2-methylbenzoyl]benzoic acid and 4,4'-bis(-dimethylamino)diphenylamine there was obtained 5-(and 6-)carboxy-3-[4-(diethylamino)-2-methylphenyl]-3-{bis[4-(dimethylamino)phenyl]amino}phthalide as a black solid, m.p.>300° C. This product developed a black image on silica gel, acidic clay and phenolic resin.

EXAMPLE 56

Following a procedure similar to that described in Example 47 but employing 3.6 g. of 4-(and 5-)carboxy-2-[4-(diethylamino)-2-methylbenzoyl]benzoic acid, 1.9 g. of diphenylamine and substituting for the pyridine 0.2 g. of urea there was obtained 4.5 g. of 5-(and 6-)carboxy-3-[4-(diethylamino)-2-methylphenyl]-3-(diphenylamino)phthalide, m.p. 265° C. (dec.).

EXAMPLE 57

Following a procedure similar to that described in Example 48 but employing 4.0 g. of 5-(and 6-)carboxy-3-[4-(diethylamino)-2-methylphenyl]-3-(diphenylamino)phthalide, 2.0 g. of potassium carbonate and dimethyl sulfate, there was obtained 1.6 g. of 5-(and 6-)methoxycarbonyl-3-[4-(diethylamino)-2-methylphenyl]-3-(diphenylamino)phthalide, m.p. 240° C. (dec.) The product developed a bluish-red image on acidic clay and phenolic resin.

EXAMPLE 58

A.

Following a procedure similar to that described in Example 53A but employing 9.6 g. (0.05 mole) of ground trimellitic anhydride, 12.1 g. (0.1 mole) of N,N-dimethylaniline and 20.0 g. (0.15 mole) of aluminum chloride there was obtained 14.5 g. of 4-(and 5-)carboxy-2-[4-(dimethylamino)benzoyl]benzoic acid, m.p.>300° C.

B.

Following a procedure similar to that described in Example 47 but employing 1.63 g. (0.005 mole) of 4-(and 5-)carboxy-2-[4-(dimethylamino)benzoyl]benzoic acid, 1.1 g. (0.005 mole) of 4-ethoxy-N-phenylaniline and 1 ml. of pyridine there was obtained 2.46 g. of 5-(and 6-)carboxy-3-[4-(dimethylamino)-phenyl]-3-[(4-ethoxyphenyl)phenylamino]phthalide, m.p. 155°-162° C. (dec.). The product developed an orange image on silica gel, acidic clay and phenolic resin.

EXAMPLE 59

Following a procedure similar to that described in Example 48 but employing 2.0 g. of 5-(and 6-)carboxy-3-[4-(dimethylamino)phenyl]-3-[(4-ethoxyphenyl)-phenylamino]phthalide, 1.0 g. of potassium carbonate and 1.5 g. of dimethyl sulfate there was obtained 1.6 g. of 5-(and 6-)methoxycarbonyl-3-[4-(dimethylamino)-phenyl]-3-[(4-ethoxyphenyl)phenylamino]-phenylamino]phthalide, m.p. 204°-210° C. The product developed an orange image on acidic clay and phenolic resin.

EXAMPLE 60

Following a procedure similar to that described in Example 47 but substituting for diphenylamine, 1.33 g. (0.005 mole) of 4,4'-bis(dimethylamino)diphenylamine there was obtained 2.5 g. of 5-(and 6-)carboxy-3-[4-(dimethylamino)phenyl]-3-{bis[4-(dimethylamino)-phenyl]amino}phthalide, m.p. 160°-170° C. (dec.). The product developed a brown image on silica gel, acidic clay and phenolic resin.

EXAMPLE 61

Following a procedure similar to that described in Example 48 but employing 2.4 g. of 5-(and 6-)carboxy-3-[4-dimethylamino)phenyl]-3-{bis[4-(dimethylamino)-phenyl]amino}-phthalide, 1.0 g. of potassium carbonate and 1.5 ml. of diethyl sulfate, there was obtained 0.24 g. of 5-(and 6-)ethoxycarbonyl-3-[4-(dimethylamino)-phenyl]-3-{bis[4-(dimethylamino)phenyl]-amino}phthalide, m.p. 73°-80° C. The product developed a brown image on acidic clay and a grape image on phenolic resin.

EXAMPLE 62

Following a procedure similar to that described in Example 47 but employing 3.1 g. of 4-(and 5-)carboxy-2-[4-(dimethylamino)benzoyl]benzoic acid and 4.0 g. of 4,4'-dioctyldiphenylamine there was obtained 6.4 g. of 5-(and 6-)carboxy-3-[4-(dimethylamino)phenyl]-3-[bis(4-octylphenyl)amino]phthalide m.p. 110°–113° C.

EXAMPLE 63

Following a procedure similar to that described in Example 48 but employing 6.0 g. of 5-(and 6-)carboxy-3-[4-(dimethylamino)phenyl]-3-[bis(4-octylphenyl)amino]phthalide, 3.0 g. of potassium carbonate and 5 ml. of dimethyl sulfate, there was obtained 5.2 g. of 5-(and 6-)methoxycarbonyl-3-[4-(dimethylamino)phenyl]-3-[bis(4-octylphenyl)amino]phthalide, m.p. 83°–89° C. The product developed a deep orange image on acidic clay and phenolic resin.

EXAMPLE 64

Following a procedure similar to that described in Example 47 but employing 3.1 g. of 4-(and 5-)carboxy-2-[4-(dimethylamino)benzoyl]benzoic acid, 1.9 g. of diphenylamine and substituting for the pyridine 0.2 g. of urea there was obtained 4.4 g. of 5-(and 6-)carboxy-3-[4-(dimethylamino)phenyl]-3-(diphenylamino)phthalide, m.p. 260° C. (dec.).

EXAMPLE 65

Following a procedure similar to that described in Example 48 but employing a 4.0 g. of 5-(and 6-)carboxy-3-[4-(dimethylamino)phenyl]-3-(diphenylamino)phthalide, 2.0 g. of potassium carbonate and dimethyl sulfate, there was obtained 2.9 g. of 5-(and 6-)methoxycarbonyl-3-[4-(dimethylamino)phenyl]-3-(diphenylamino)phthalide, m.p. 250° C. (dec.). The product developed an orange image on acidic clay and phenolic resin.

EXAMPLE 66

Following a procedure similar to that described in Example 2 but employing 5.4 g. of 2-[4-(dimethylamino)benzoyl]-benzoic acid, 6.8 g. of N-phenyl-4-(p-toluenesulfonamido)aniline and 1.0 g. of urea there was obtained 9.05 g. of 3-[4-(dimethylamino)phenyl]-3-{[4-p-toleunesulfonamido)phenyl]phenylamino}-phthalide, m.p. 116°–118° C. The product developed an orange image on acidic clay and phenolic resin.

EXAMPLE 67

Following a procedure similar to that described in Example 2 but employing 6.3 g. of 2-[4-(diethyamino)-2-methylbenzoyl]benzoic acid, 6.8 g. of N-phenyl-4-(p-toluenesulfonamido)-aniline and 1.0 g. of urea there was obtained 11.3 g. of 3-[4-(diethylamino)-2-methylphenyl]-3-{[4-(p-toluenesulfonamido)-phenyl]-phenylamino}phthalide, m.p. 91°–110° C. The product developed a red image on acidic clay and phenolic resin.

It is contemplated that by following procedures similar to those described in Examples 1, 2, 3, 4 and 5 but employing the appropriate 2-substituted diarylamines of Formula IV there will be obtained the phthalides of Formula II, Examples 68–100 presented in Table A hereinbelow.

TABLE A

| Phthalides of Formula II | | | | | | |
|---|---|---|---|---|---|---|
| Ex. | $Q_4$ | $Q_5$ | $Q_6$ | $Q_7$ | $R_1$ | $R_2$ | $R_3$ |
| 68 | H | H | H | H | n-$C_4H_9$ | $CH_3$ | $CH_3$ |
| 69 | H | $(C_2H_5)_2N$ | H | H | H | $CH_3$ | $C_6H_5CH_2$ |
| 70 | H | Br | H | H | Br | $CH_3$ | $CH_3$ |
| 71 | Br | Br | Br | Br | $(CH_3)_2N$ | $CH_3$ | $CH_3$ |
| 72 | H | H | H | H | $C_2H_5O$ | $C_2H_5$ | $C_2H_5$ |
| 73 | H | $(C_4H_9)_2N$ | H | H | H | $CH_3$ | $C_2H_5$ |
| 74 | H | H | F | H | H | $CH_3$ | $C_6H_5$ |
| 75 | H | Cl | H | H | H | t-$C_4H_9$ | t-$C_4H_9$ |
| 76 | F | F | F | F | H | $CH_3$ | p-$CH_3C_6H_4$ |
| 77 | H | H | H | H | $(sec-C_4H_9)_2N$ | sec-$C_4H_9$ | sec-$C_4H_9$ |
| 78 | I | I | I | I | H | $CH_3$ | $CH_3$ |
| 79 | H | H | H | H | I | $C_4H_9$ | p-$C_4H_9$—$C_6H_4$ |
| 80 | H | H | $(C_2H_5)_2N$ | H | H | $C_2H_5$ | $C_4H_9$ |
| 81 | H | H | $(C_4H_9)_2N$ | H | H | $CH_3$ | $CH_3$ |
| 82 | H | H | H | H | $(CH_3)_2CHCH_2O$ | $CH_3$ | $CH_3$ |
| 83 | H | H | H | H | H | $CH_3$ | $CH_3$ |
| 84 | H | —$CO_2CH_2C_6H_5$ | H | H | H | $CH_3$ | $CH_3$ |
| 85 | H | H | —$CO_2C_8H_{17}$ | H | $C_2H_5$ | $C_2H_5$ | $C_2H_5$ |
| 86 | H | —$CO_2C_{18}H_{37}$ | H | H | Cl | $CH_3$ | $CH_3$ |
| 87 | H | —$CO_2C_{14}H_{29}$ | H | H | H | $CH_3$ | $CH_3$ |
| 88 | H | H | —$CO_2(CH_2)_8CH(CH_3)CH_3$ | H | $CH_3$ | $C_2H_5$ | $C_2H_5$ |
| 89 | H | $CO_2H$ | H | H | H | $CH_3$ | $CH_3$ |
| 90 | H | H | H | H | H | $CH_3$ | $CH_3$ |
| 91 | H | H | H | H | $CH_3$ | $C_2H_5$ | $C_2H_5$ |
| 92 | Cl | Cl | Cl | Cl | H | $CH_3$ | $CH_3$ |
| 93 | H | H | H | H | $CH_3$ | $C_2H_5$ | $C_2H_5$ |
| 94 | H | H | H | H | $CH_3$ | $C_2H_5$ | $C_2H_5$ |
| 95 | H | —$CO_2^\ominus Na^\oplus$ | H | H | H | $CH_3$ | $CH_3$ |
| 96 | H | H | —$CO_2^\ominus NH_4^\oplus$ | H | H | $CH_3$ | $CH_3$ |
| 97 | H | —$CO_2^\ominus HN^\oplus(C_2H_5)_3$ | H | H | H | $C_2H_5$ | $C_6H_5CH_2$ |
| 98 | H | —$CO_2^\ominus H_3N^\oplus C_{18}H_{37}$ | H | H | $CH_3$ | $C_2H_5$ | $C_2H_5$ |
| 99 | H | H | —$CO_2^\ominus H_3N^\oplus C_8H_{17}$ | H | H | $CH_3$ | $CH_3$ |
| 100 | H | H | H | H | $CH_3$ | $C_2H_5$ | $C_2H_5$ |

TABLE A-continued

Phthalides of Formula II

| Ex. | Y₁ | Y₂ | Y₃ | Y₄ |
|---|---|---|---|---|
| 68 | H | H | 3-I | H |
| 69 | H | H | 2-$C_2H_5$ | H |
| 70 | H | H | 4-Br | H |
| 71 | H | H | 3-(t-$C_4H_9$) | H |
| 72 | 2-$CH_3$ | H | 4-$CH_3O$ | H |
| 73 | 3-Br | H | 5-Br | H |
| 74 | H | H | 2-F | H |
| 75 | 2-Cl | H | 4-F | H |
| 76 | 3-$CH_3O$ | H | 3-$CH_3O$ | H |
| 77 | H | H | H | H |
| 78 | H | H | 4-OH | H |
| 79 | 3-$CH_3$ | 4-$CH_3$ | 3-$CH_3$ | 4-$CH_3$ |
| 80 | 3-$C_4H_9O$ | H | 3-$C_4H_9O$ | H |
| 81 | H | H | 3-$C_2H_5$–C(CH$_3$)$_2$– | H |
| 82 | 2-Cl | 4-Cl | 2-Cl | 4-Cl |
| 83 | H | H | 4-$NHSO_2C_6H_5$ | H |
| 84 | 4-$CH_2C_6H_5$ | H | H | H |
| 85 | 2-$CO_2C_4H_9$ | H | H | H |
| 86 | 4-CHCH$_2$C$_6$H$_5$ (CH$_3$) | H | H | H |
| 87 | 2-$CO_2C_2H_5$ | H | H | H |
| 88 | 4-$CO_2CH_3$ | H | H | H |
| 89 | 2-$CO_2H$ | H | H | H |
| 90 | 4-$NH_2$ | H | H | H |
| 91 | 4-$NH_2$ | H | 4-$NH_2$ | H |
| 92 | 4-$NHC_4H_9$ | H | 4-$NHC_4H_9$ | H |
| 93 | 4-NH–(cyclohexyl) | H | H | H |
| 94 | 4-$NHCOC_4H_9$ | H | 4-$NHCOC_4H_9$ | H |
| 95 | 4-$OC_2H_5$ | H | H | H |
| 96 | H | H | H | H |
| 97 | 4-$OC_2H_5$ | H | H | H |
| 98 | H | H | H | H |
| 99 | 4-$OC_2H_5$ | H | H | H |
| 100 | 4-$NHCH(CH_3)_2$ | H | H | H |

EXAMPLE 101

The color formers of Examples 2 and 7 were microencapsulated as follows. A solution containing 1 g. of the color former in 49 g. of isopropylbiphenyl and a solution containing 5 g. of carboxymethylcellulose in 200 ml. of water were mixed and emulsified by rapid stirring. The desired particle size (5 microns) was checked by microscope. To the emulsion was added a solution containing 15 g. of pigskin gelatin in 120 ml. of water. The pH was adjusted to 6.5 with 10% aqueous sodium hydroxide with rapid stirring, and following the gradual addition of 670 ml. of water with heating (at 50° C.) the pH was adjusted to 4.5 with 10% aqueous acetic acid with continued rapid stirring. After 5 minutes 10 g. of 25% aqueous glutaraldehyde was added and rapid stirring was continued an additional 15 minutes. The resulting microcapsule dispersion was stirred more slowly overnight.

Starch (12 g.) was gradually added to 60 ml. of water. The mixture was heated to 90° C. and stirred 15 minutes. After cooling to room temperature the mixture was added to 473 g. of the above microcapsule dispersion and the resulting emulsion stirred vigorously for 2 minutes, and then coated on white typewriter paper sheets (0.0015 in. film thickness). The sheets were air dried. Duplicate typewritten images were made on receiving sheets coated with either phenolic resin or acidic clay. The color former of Example 2 produced an orange image on both types of receiving sheets, and the color former of Example 7 produced a red image on both types of receiving sheets.

EXAMPLE 102

Polyvinyl alcohol dispersions of the color formers of Examples 2, 3 and 7 were prepared by shaking 1 hour on a paint shaker a mixture containing 2.0 g. of the color former, 3.7 g. of water, 8.6 g. of 10% aqueous polyvinyl alcohol and 10 g. of zirconium grinding beads. A polyvinyl alcohol dispersion of bisphenol A was prepared by shaking a mixture containing 9.8 g. of bisphenol A, 18.2 g. of water, 42 g. of 10% aqueous polyvinyl alcohol and 70 ml. of zirconium grinding beads. The coating mixture was made by combining and thoroughly mixing 2.1 g. of the polyvinyl alcohol dispersion of the color former with 47.9 g. of the polyvinyl alcohol dispersion of bisphenol A. The coating mixture was applied (at thicknesses of 0.003 in. and 0.0015 in.) to white mimeo paper sheets and the sheets were dried at room temperature. Contacting the coated sheets with a heated stylus at a temperature between 110° C. and 150° C. produced a dark orange image on the sheet coated with the color former of Example 2, a dark red image on the sheet coated with the color former of Example 3 and a dark purple image on the sheet coated with the color former of Example 7.

EXAMPLE 103

Following a procedure similar to that described in Example 101 but substituting kerosene for isopropylbiphenyl the color former of Example 32 was microencapsulated and coated on a transfer sheet. The color former developed a red image on both types of receiving sheets.

EXAMPLE 104

Following a procedure similar to that described in Example 101 but omitting the addition of starch to the microcapsule dispersion, the color former of Example 43 was microencapsulated and coated on a transfer sheet. The color former developed a black image on both types of receiving sheets. The image formed on the clay-coated receiving sheet turned green on standing.

EXAMPLE 105

Following a procedure similar to that described in Example 101 but omitting the addition of starch to the microcapsule dispersion, a mixture containing 0.876 g. of the color former of Example 16 and 0.584 g. of crystal violet lactone was microencapsulated and coated on a transfer sheet. The mixture of color formers developed a blue to black image on resin-coated receiving sheets.

We claim:

1. A process for producing a compound having the formula

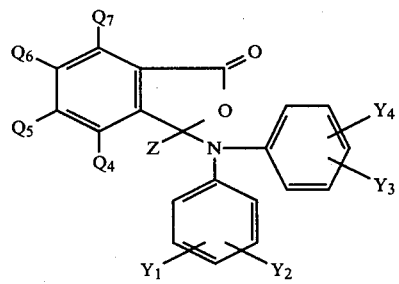

which comprises reacting a 2-substituted benzoic acid having the formula

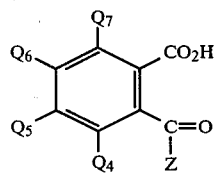

with a diarylamine having the formula

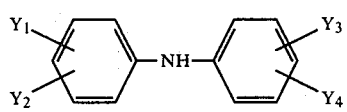

in the presence of the anhydride of an alkanoic acid having from 2 to 5 carbon atoms and an organic base, wherein in the above formulas:

$Q_4$ is hydrogen or halo;

$Q_5$ is the same as $Q_4$; or di-lower-alkylamino, halo or COX when $Q_4$, $Q_6$ and $Q_7$ are each hydrogen;

$Q_6$ is the same as $Q_4$; or di-lower-alkylamino, halo or COX when $Q_4$, $Q_5$ and $Q_7$ are each hydrogen;

$Q_7$ is the same as $Q_4$;

X is hydroxyl, benzyloxy or alkoxy having from 1 to 18 carbon atoms;

Z is a radical having the formula

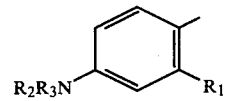

in which:

$R_1$ is selected from the group consisting of hydrogen, halo, lower-alkyl, lower-alkoxy and di-lower-alkylamino;

$R_2$ is lower-alkyl; and $R_3$ is selected from the group consisting of lower-alkyl, benzyl, phenyl and phenyl substituted with a lower-alkyl or lower-alkoxy group; and $Y_1$, $Y_2$, $Y_3$ and $Y_4$ are the same or different and are selected from the group consisting of hydrogen, halo, hydroxyl, lower-alkoxy, alkyl having from 1 to 9 carbon atoms, phenyl-lower-alkyl, $COOR_4$ and $NR_5R_6$ where $R_4$ and $R_5$ are hydrogen or lower-alkyl and $R_6$ is hydrogen, lower-alkyl, cycloalkyl having from 5 to 7 carbon atoms, lower-alkanoyl, phenylsulfonyl or lower-alkyl-substituted phenylsulfonyl.

2. A process according to claim 1 wherein said anhydride of an alkanoic acid having from 2 to 5 carbon atoms is acetic anhydride and said organic base is selected from the group consisting of said diarylamine, pyridine and urea.

3. A process for producing a compound having the formula

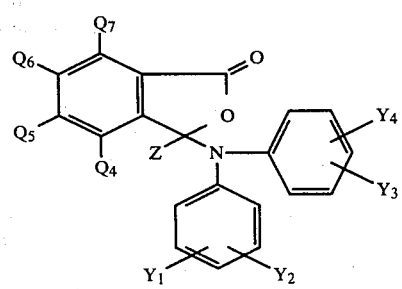

which comprises reacting a 2-substituted benzoic acid having the formula

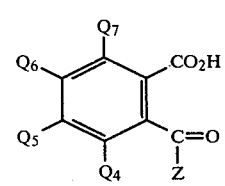

with a diarylamine having the formula

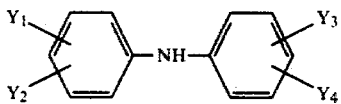

in the presence of the anhydride of an alkanoic acid having from 2 to 5 carbon atoms and an organic base, wherein in the above formulas:

$Q_4$, $Q_5$, $Q_6$ and $Q_7$ are hydrogen;

Z is 9-julolidinyl; and $Y_1$, $Y_2$, $Y_3$ and $Y_4$ are the same or different and are selected from the group consisting of hydrogen, lower-alkoxy and alkyl having from 1 to 9 carbon atoms.

4. A process according to claim 3 wherein said anhydride of an alkanoic acid having from 2 to 5 carbon atoms is acetic anhydride and said organic base is selected from the group consisting of said diarylamine, pyridine and urea.

5. 4-Carboxy-2-[2-ethoxy-4-(dimethylamino)benzoyl]benzoic acid.

6. 5-Carboxy-2-[2-ethoxy-4-(dimethylamino)benzoyl]benzoic acid.

* * * * *

UNITED STATES PATENT AND TRADEMARK OFFICE
CERTIFICATE OF CORRECTION

PATENT NO. : 4,255,577  
DATED : March 10, 1981  
INVENTOR(S) : Paul J. Schmidt and William M. Hung Page 1 of 2

It is certified that error appears in the above-identified patent and that said Letters Patent is hereby corrected as shown below:

Column 2, first formula,

"
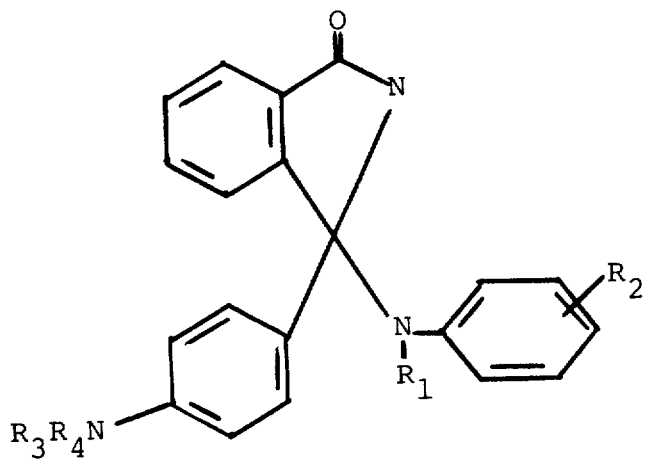
" should read

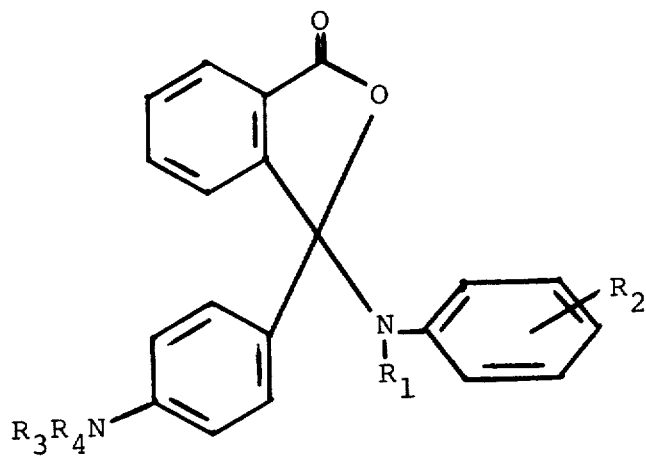

-- --.

UNITED STATES PATENT AND TRADEMARK OFFICE
CERTIFICATE OF CORRECTION

PATENT NO. : 4,255,577

DATED : March 10, 1981

INVENTOR(S) : Paul J. Schmidt and William M. Hung

It is certified that error appears in the above-identified patent and that said Letters Patent is hereby corrected as shown below:

Column 2, lines 63-64, "disubstitutedamino] or" should read -- disubstituted-amino]phenyl or --.

Signed and Sealed this

Seventh Day of January 1986

[SEAL]

Attest:

*Attesting Officer*

DONALD J. QUIGG

*Commissioner of Patents and Trademarks*